US012678061B2

(12) United States Patent
Yoshizawa et al.

(10) Patent No.: US 12,678,061 B2
(45) Date of Patent: Jul. 14, 2026

(54) APPARATUS, METHOD, AND NON-TRANSITORY COMPUTER-READABLE RECORDING MEDIUM HAVING STORED THEREIN PROGRAM FOR BLOOD PRESSURE ESTIMATING PROGRAM

(71) Applicant: TOHOKU UNIVERSITY, Sendai (JP)

(72) Inventors: Makoto Yoshizawa, Sendai (JP); Norihiro Sugita, Sendai (JP); Taihei Noro, Sendai (JP); Taiki Ikemiya, Sendai (JP)

(73) Assignee: TOHOKU UNIVERSITY, Sendai (JP)

( * ) Notice: Subject to any disclaimer, the term of this patent is extended or adjusted under 35 U.S.C. 154(b) by 735 days.

(21) Appl. No.: 17/541,463

(22) Filed: Dec. 3, 2021

(65) Prior Publication Data

US 2022/0087550 A1 Mar. 24, 2022

Related U.S. Application Data

(63) Continuation of application No. PCT/JP2020/021822, filed on Jun. 2, 2020.

(30) Foreign Application Priority Data

Jun. 4, 2019 (JP) ................................. 2019-104885

(51) Int. Cl.
*A61B 5/021* (2006.01)
(52) U.S. Cl.
CPC .............................. *A61B 5/02116* (2013.01)
(58) Field of Classification Search
None
See application file for complete search history.

(56) References Cited

U.S. PATENT DOCUMENTS

2008/0249382 A1* 10/2008 Oh ....................... A61B 5/0245
600/509
2010/0274143 A1 10/2010 Kim et al.
(Continued)

FOREIGN PATENT DOCUMENTS

CN 101773387 A 7/2010
JP 2014-198198 A 10/2014
(Continued)

OTHER PUBLICATIONS

International Search Report of the International Searching Authority issued by Japan Patent Office for International Patent Application No. PCT/JP2020/021822, mailed on Aug. 11, 2020.
(Continued)

*Primary Examiner* — Jennifer Robertson
*Assistant Examiner* — Om Patel
(74) *Attorney, Agent, or Firm* — Myers Wolin, LLC

(57) ABSTRACT

An apparatus for estimating a blood pressure includes a first pulse wave information detector configured to detect first pulse wave information at a first position of a living body, a second pulse wave information detector configured to detect second pulse wave information at a second position of the living body, the second position being spaced a distance in a vertical direction from the first position; and a blood pressure estimator configured to estimate, based on pulse wave amplitude information at the first position and the second position obtained from the first pulse wave information obtained by the first pulse wave information detector and the second pulse wave information obtained by the second pulse wave detector and the distance in the vertical direction, a blood pressure of the living body.

10 Claims, 7 Drawing Sheets

(56) References Cited

U.S. PATENT DOCUMENTS

| | | | | |
|---|---|---|---|---|
| 2013/0218028 | A1* | 8/2013 | Mestha | A61B 5/0075 |
| | | | | 600/479 |
| 2015/0327786 | A1 | 11/2015 | Lading et al. | |
| 2015/0366456 | A1 | 12/2015 | Takamori et al. | |
| 2017/0224227 | A1* | 8/2017 | Kitagawa | A61B 5/02108 |
| 2017/0354334 | A1* | 12/2017 | Tarassenko | A61B 5/742 |
| 2018/0078155 | A1 | 3/2018 | Baek et al. | |

FOREIGN PATENT DOCUMENTS

| | | | | |
|---|---|---|---|---|
| JP | 6072893 | B2 | 2/2017 | |
| WO | WO-2019202319 | A1 * | 10/2019 | A61B 5/02125 |

OTHER PUBLICATIONS

Sugita et al., "Contactless Technique for Measuring Blood Pressure Variability from One Region in Video Plethysmography", Journal of Medical and Biological Engineering, Mar. 28, 2018, ISSN 1609-0985, DOI 10.1007/s40846-018-0388-8, Springer, Taiwan.

Gavish et al., "Arterial Stiffness: Going a Step Beyond", American Journal of Hypertension, Nov. 2016, pp. 1223-1233, vol. 29(11), doi:10.1093/ajh/hpw061, USA.

Notice of Reasons for Refusal issued by the Japan Patent Office for corresponding Japanese Patent Application No. 2021-521083, mailed May 18, 2021, with a full English translation.

Decision of Refusal issued by the Japan Patent Office for corresponding Japanese Patent Application No. 2021-521083, mailed Sep. 7, 2021, with a full English translation.

International Preliminary Report on Patentability with English translation of the Written Opinion of the International Searching Authority issued by The International Bureau of WIPO for corresponding International Patent Application No. PCT/JP2020/021822, dated Dec. 7, 2021.

First Office Action issued by the China National Intellectual Property Administration for corresponding Chinese Patent Application No. 202080041566.2, dated Feb. 2, 2024, with an English translation.

The second Examination Opinion Notice issued by the China National Intellectual Property Administration for corresonding Chinese Patent Application No. 202080041566.2, dated Sep. 5, 2024, with an English translation of relevant parts.

* cited by examiner

| $R$ | $P'=qh/(1-R)$ |
|---|---|
| $R_1$ | $P'_1$ |
| $R_2$ | $P'_2$ |
| . | . |
| . | . |
| . | . |
| $R_n$ | $P'_n$ |

M2

| $\alpha$ |
|---|
| $\alpha_1$ |
| $\alpha_2$ |
| . |
| . |
| . |
| $\alpha_i$ |

APPARATUS, METHOD, AND NON-TRANSITORY COMPUTER-READABLE RECORDING MEDIUM HAVING STORED THEREIN PROGRAM FOR BLOOD PRESSURE ESTIMATING PROGRAM

CROSS-REFERENCE TO RELATED APPLICATION

This application is a continuation application of International Application No. PCT/JP2020/021822, filed on Jun. 2, 2020 and designated the U.S., which claims priority to Japanese Patent application No. 2019-104885, filed on Jun. 4, 2019, the entire contents of each are incorporated herein by reference.

FIELD

The present disclosure relates to an apparatus, a method, and a non-transitory computer-readable recording medium having stored therein program for blood pressure estimating.

BACKGROUND

Conventionally, a blood pressure has been measured with a contact-type sensor worn on the body. However, in such a conventional method, since the wearing of the sensor annoys the wearer and the blood pressure measurement needs to be performed consciously, it is difficult to make the blood pressure measurement customary, and it is impossible to measure the blood pressure of an unspecified person other than the sensor wearer.

As a solution to the above, in recent years, methods have been proposed which each remotely and contactlessly obtains a pulse wave signal from a video signal obtained by photographing a body with a video camera (Patent Document 1 and Non-Patent Document 1). Specifically, these methods each extracts a video pulse wave signal by signal processing the brightness value of the body video signal over multiple frames and calculates a numerical value correlated with a blood pressure. In particular, the method of Patent Document 1 calculates, as a value correlated with a blood pressure, a phase difference between a video pulse wave signal at a part (proximal part) of the body near the heart and a video pulse wave signal at the part (distal part) far from the heart. The method of Non-Patent Document 1 calculates, as a value correlated with a blood pressure, a difference between a boundary time from the diastolic to the systolic of a video pulse wave of a freely-selected part of the body and the time at which the extreme value of a basic wave of the video pulse wave is given.

[Patent Document 1] Japanese Patent No. 6072893 Non-Patent Document

[Non-Patent Document 1] Norihiro Sugita, Makoto Yoshizawa, Makoto Abe, Akira Tanaka, Noriyasu Homma, Tomoyuki Yambe: Contactless technique for measuring blood-pressure variability from one region in video plethysmography, Journal of Medical and Biological Engineering. pp. 1-10, (2018) https://doi.org/10.1007/s40846-018-0388-8.

In the techniques of the above-mentioned document, although it is possible to obtain a value correlated with the blood pressure, it is necessary to obtain, in order to estimate the absolute value of the blood pressure from the correlation value of the blood pressure, a parameter (regression coefficient or bias) which gives a regression expression of both. Here, the "absolute value" does not mean a mathematical meaning of a numerical value corresponding to a distance from the origin, but a value having an original unit of a measured quantity as a synonym of a "relative value". However, these parameters differ from a subject, and in order to obtain these parameters, it is necessary to estimate these parameters based on a true blood pressure value obtained by using a conventional contact-type sensor under a situation in which blood pressure fluctuation on each subject is generated by some method, which requires complicated many processing steps.

As one example, in the method using pulse wave propagation velocity of a pulse wave, information in the time axis direction becomes indispensable in order to obtain a time difference and a phase difference. However, obtaining of such time information requires a high-performance CPU and a complicated program processing for analyzing pulse wave and has a difficulty in obtaining a precise value.

The apparatus, the method, and the program for estimating a blood pressure of the present disclosure have been devised in view of the problems as described above, and provide novel apparatus, method, and program for estimating a blood pressure capable of directly estimating an absolute value of a blood pressure from a pulse wave signal even if there is no information in the time axis direction such as a phase difference of a pulse wave.

SUMMARY

An apparatus for estimating a blood pressure comprising:
a first pulse wave information detector configured to detect first pulse wave information at a first position of a living body;
a second pulse wave information detector configured to detect second pulse wave information at a second position of the living body, the second position being spaced a distance in a vertical direction from the first position; and
a blood pressure estimator configured to estimate, based on pulse wave amplitude information at the first position and the second position obtained from the first pulse wave information obtained by the first pulse wave information detector and the second pulse wave information obtained by the second pulse wave detector and the distance in the vertical direction, a blood pressure of the living body.

BRIEF DESCRIPTION OF DRAWINGS

FIG. 3 is a flow chart illustrating a procedure of estimating a blood pressure;

FIG. 7 is a diagram illustrating another embodiment.

DESCRIPTION OF EMBODIMENT(S)

Hereinafter, an apparatus, a method, and a program for estimating a blood pressure according to embodiments of the present disclosure will now be described with reference to the accompanying drawings. However, the embodiments described below are merely illustrative and there is no intention to exclude the application of various modifications and techniques that are not explicitly described below. For example, the present embodiment can be variously modified and implemented without departing from the scope thereof.

1. HARDWARE CONFIGURATION

Figure 1:
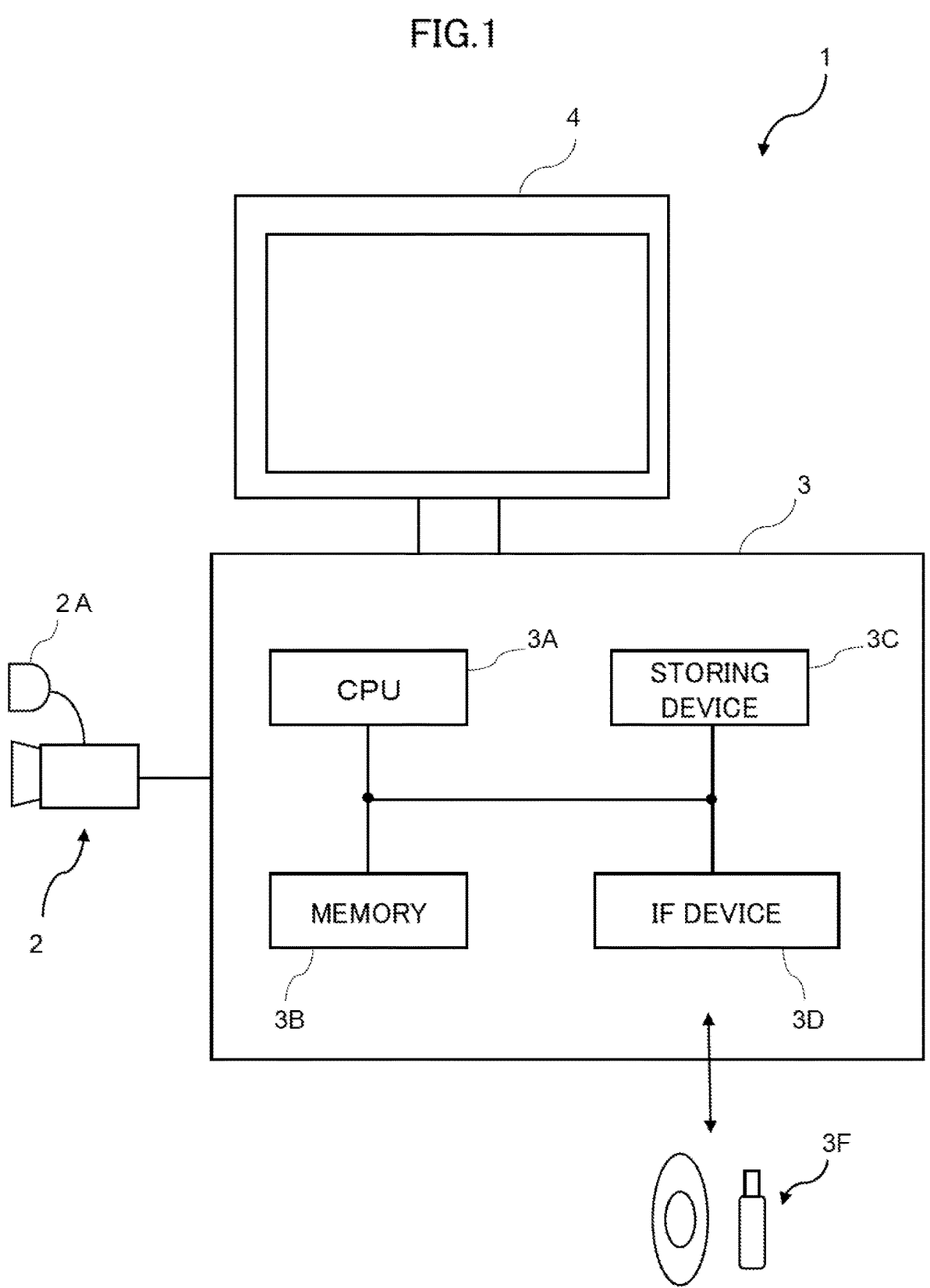
FIG. 1 is a block diagram illustrating a hardware configuration of an apparatus for estimating a blood pressure according to an embodiment.

First, description will now be made in relation to an example of a hardware configuration of a blood pressure estimating device of an embodiment with reference to FIG. 1. As illustrated in FIG. 1, the blood pressure estimating device 1 of the embodiment includes a video obtaining device 2, an information processing device 3, and an outputting device 4. The video obtaining device 2 and the output apparatus 4 are both communicably connected to the information processing device 3 wiredly or wirelessly. The blood pressure estimating device 1 may further include an inputting device (not illustrated) such as a mouse, a keyboard, and/or an operation button.

<Video Obtaining Device>

The video obtaining device 2 is a device that photographs a predetermined part of a body of a living body (hereinafter, also referred to as a subject) in a non-contact state, and acquires video information (video signal) continuous in time series. In the embodiment, a visible light camera having a photographing lens and a visible-light video capturing device that receives visible light is shown as an example of video obtaining device 2. The video obtaining device 2 is not limited thereto and alternatively may be an infrared light camera. The video obtaining device 2 outputs the obtained video signal to the information processing device 3.

The video obtaining device 2 may further include a lighting device 2A, which is selected according to the type of the video capturing device.

The predetermined part of the body of the subject to be photographed by the video obtaining device 2 is not particularly limited, but is preferably a part of the skin surface whose video can be easily taken because of being usually largely exposed, for example a hand and a face. Above all, the palm, the forehead, and the cheeks are preferably used in view of the size of the video taking region. In particular, from the viewpoint of easiness in obtaining a video pulse wave having a high signal-to-noise ratio of a signal, a part in which the arteriole rises the peripheral vascular resistance under control of the sympathetic nerve when the blood pressure rises is preferable. Such a part may be a peripheral part such as a limb such as hands or legs, and among these, a hand is preferable, and a palm of a hand is more preferable.

The number of videos obtaining devices 2 is not particularly limited. A necessary predetermined part may be extracted from a video from one video obtaining device 2, or may be captured by multiple videos obtaining devices 2. When multiple videos obtaining devices 2 are used, the lighting device 2A may be attached to each individual video obtaining device 2 or may be shared by the multiple videos obtaining devices 2.

<Information Processing Device>

The information processing device 3 is composed of a computer such as a Personal Computer (PC) or a server. The information processing device 3 processes a video signal received from the video obtaining device 2, and outputs the processed video signal to the output apparatus 4. The information processing device 3 includes a Central Processing Unit (CPU) 3A, a memory 3B, a storing device 3C, and an interface device 3D, which are communicably connected to each other via a bus.

<CPU>

The CPU 3A is an example of an arithmetic processing device (processor) that performs various controls and operations. The CPU 3A can achieve the function of the blood pressure estimating device 1 by expanding program for estimating a blood pressure stored in the storing device 3C, which will be described below, in the memory 3B and executing the expanded program.

The program for estimating a blood pressure referred to herein is a program for causing the computer (CPU 3A) to execute a process of detecting first pulse wave information at a first position of the living body (subject), detecting second pulse wave information at a second position distant in the vertical direction from the first position of the living body, and estimating the blood pressure of the living body based on the compared value information between the first pulse wave information and the second pulse wave information.

Embodiments of the first position and the second position of the living body, the first pulse wave information and the second pulse wave information, and the compared value information will be described below.

<Memory>

The memory 3B and the storing device 3C are storage devices that store various types of data and programs.

The memory 3B or the storing device 3C can store the program for estimating a blood pressure or the like that achieves all or part of various functions of the information processing device 3.

The interface (IF) device 3D is a communication interface that controls the connection and communication between, for example, the network, the information processing device 3, the video obtaining device 2, and the outputting device 4 wirelessly or wiredly. The program for estimating a blood pressure may be downloaded from a network (not shown) to the CPU 3A via the IF and stored in the storing device 3C.

The IF device 3D may include a reader (not shown) that reads data or a program recorded in a recording medium 3F. The reader may include a connection terminal or a device to which the computer-readable recording medium 3F can be connected or inserted.

A program for estimating a blood pressure may be stored in the recording medium 3F.

<Outputting Device>

The outputting device 4 is a device that provides information mainly through vision. The outputting device 4 displays, for example, a video obtained by the video obtaining device 2, the result of processing performed by the information processing device 3.

As the outputting device 4, a mobile terminal such as a smart phone can be used. In this case, the output from the information processing device 3 is transmitted from the information processing device 3 to the mobile terminal through the communication network via the IF device 3D, and the output result is displayed on the display of the mobile terminal.

2. PRINCIPLES

In a living body, blood pressure in each part of the body fluctuates in synchronization with heartbeats. This fluctuation generates a pulse pressure (a difference between the maximum and minimum blood pressures) for each beat. Although, strictly speaking, being different depending on the hardness of the blood vessel at the respective parts, the pulse pressure can be assumed to be equal at respective parts of the body irrespective of the height of the parts.

On the other hand, in the living body, the pulse wave at each part of the body also fluctuates in synchronization with the heartbeat. This fluctuation generates a difference between the maximum and minimum values for each beat (the difference between the peak of the maximum value and the bottom of the minimum value, hereinafter simply referred to as "pulse wave amplitude"). This pulse wave amplitude varies with the vertical position of the body. It has been also known that a relationship of a blood pressure to a blood vessel cross-sectional area related to a pulse wave amplitude can be approximated by an exponential function having a bias coefficient related to the characteristic of the blood vessel as to be detailed below.

As a result of enthusiastic development on the basis of the above findings, the inventor(s) of the present application successfully reached a conclusion that a coefficient being related to a blood pressure and being correlated with a curvature of a change in pulse wave amplitude is defined in terms of vertical positions of the respective parts of the body. The bias coefficient, which is the only unknown number in this derivation, varies for each individual person, but a rough value thereof has been known as a literature value. Using the literature value makes it possible to estimate a rough blood pressure value, which is a landmark that eliminates the need for a true value of the blood pressure of a subject. Further, even if a precise bias coefficient with higher accuracy is to be obtained for each individual subject, a single true value of a blood pressure suffices to obtain a blood pressure value without giving the subject fluctuation of a blood pressure.

On the basis of the above, the absolute value of a blood pressure could be estimated directly from the pulse wave by using a relationship between the height information of at least two measurement positions having a height difference in vertical direction and the pulse wave amplitude J of the pulse wave signal measured at each of the positions.

Hereinafter, description will now be made in relation to the specific principle and an embodiment constructed based on the principle.

<Relationship between Blood Pressure P and Blood Vessel Cross-sectional Area A>

One of the previous studies Benjamin Gavish: Arterial stiffness: Going a step beyond, American Journal of Hypertension (2016)) have shown that a blood vessel pressure P [mmHg] and the cross-sectional area A [cm$^2$] of a blood vessel have a relationship represented by Expression (1).

[Expression 1]

$$P = \alpha + \gamma e^{\beta A} \qquad (1)$$

Here, the symbol $\alpha$ is a bias coefficient related to the characteristic of a blood vessel, the symbol $\beta$ is a value representing the intensity of a distortion (related to the increase in the volume pulse wave) of a pulse wave, the symbol $\gamma$ is a weighting coefficient that correlates $\alpha$ with $\beta$. The values $\alpha$, $\beta$, and $\gamma$ are constants, but change with characteristic of the blood vessel. The characteristic of blood vessels is age dependent, as shown in Table 1, especially because arteriosclerosis is age dependent. The characteristic of blood vessels changes with other factors except for age, and largely different with individuals, and it is considered that the characteristic of the same person may change due to various state such as intraday fluctuation, exercise, and psychological tension. Hereinafter, Expression (1) is referred to as a basic function. That is, this basic function can be regarded as a function including the bias coefficient $\alpha$ that depends on the age of the living body and representing the relationship between the blood pressure P of the living body and the blood vessel cross-sectional area A.

TABLE 1

| Average values of parameters $\alpha$, $\beta$, and $\gamma$ of basic function | | |
| --- | --- | --- |
| | Younger adult (Age 28-31) | Elderly (Age 71-78) |
| $\alpha$ [mmHg] | 53 | 43 |
| $\beta$ [cm$^{-2}$] | 1.43 | 3.42 |
| $\gamma$ [mmHg] | 1.07 | 1.05 |

<Relationship between Signal Value I of Video Pulse Wave and Blood Vessel Cross-sectional Area A>

A pulse wave (video pulse wave, Video Plethysmogram: VPG) obtained from a video signal is used for obtaining pulsation information in the blood vessel from the video signal obtained by photographing the skin by utilizing the property that the hemoglobin contained in blood absorbs green light well, or the like. The amount of hemoglobin in the arterial vessels increases and decreases periodically with the heartbeat and is proportional to the volume of the arterial vessels. Since the amount of hemoglobin is a generation factor of a video pulse wave, it is estimated that the video pulse wave is also proportional to the volume of the arterial blood vessel (blood vessel cross-sectional area A). This property is the same for infrared light. Therefore, the relationship between the signal value I of a video pulse wave and the vessel cross-sectional area A can be expressed by using the proportional constant KB as in Expression (2) (where, the symbol K is a constant including various factors affecting the pulse wave signal (e.g., lighting environment at the time of measurement)).

[Expression 2]

$$I = K\beta A \qquad (2)$$

When the Expression (2) is transformed and then substituted into the Expression (1), the expression can be transformed into the Expression (3).

[Expression 3]

$$\frac{P - \alpha}{\gamma} = e^{I/K} \qquad (3)$$

<Relationship between Blood Pressure P and Pulse Wave Amplitude J>

The natural logarithm of the Expression (3) is expressed by Expression (4).

[Expression 4]

$$I = K \ln\left(\frac{P - \alpha}{\gamma}\right) = K \ln(P - \alpha) - K \ln \gamma \qquad (4)$$

Figure 4:
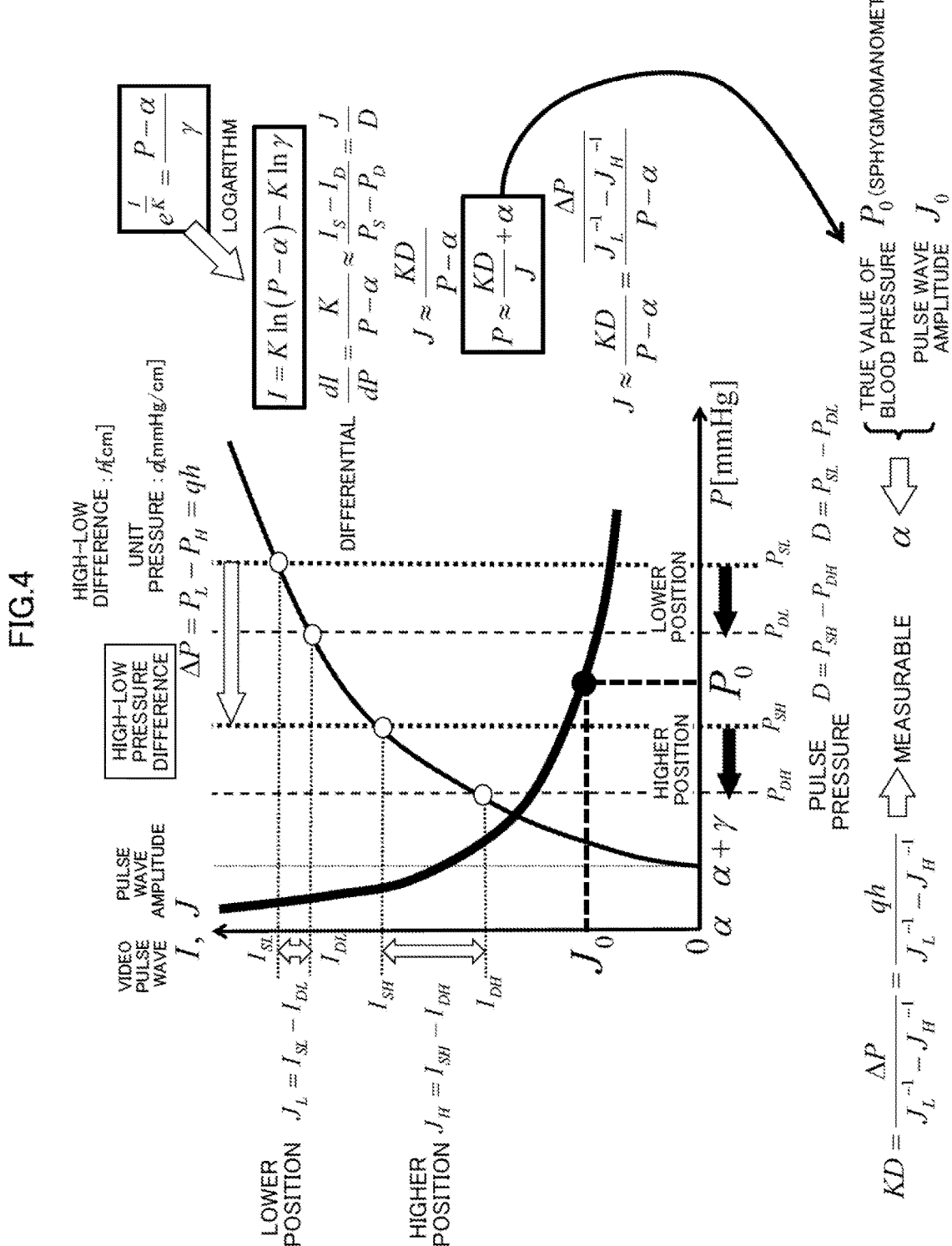
FIG. 4 is a diagram illustrating the embodiment.

The relationship of Expression (4) is illustrated by the thin solid line in FIG. 4.

Differentiating Expression (4) with respect to P yields Expression (5).

[Expression 5]

$$\frac{dI}{dP} = \frac{K}{P - \alpha} \tag{5}$$

The differentiation of a signal value of a video pulse wave with respect to a blood pressure can also be approximated by the ratio of the difference (pulse wave amplitude) of the systolic and diastolic pulse wave signal values to the difference (pulse pressure) of the systolic and diastolic blood pressures. That is, when it is assumed that the systolic blood pressure (maximum blood pressure) at each beat is represented by $P_S$; the diastolic blood pressure (minimum blood pressure) is represented by $P_D$; the pressure gradient (pulse pressure) between the systolic and diastolic pressure gradient is represented as the $D = P_S - P_D$; the systolic and diastolic pulse wave signal values corresponding to a blood pressure are represented by $I_S$, $I_D$, respectively; and the difference between the systolic and diastolic pulse wave signals (difference between maximum and minimum values within a beat, i.e., pulse wave amplitude) is represented as the $J = I_S - I_D$; and differentiation of a signal value of a video pulse wave with respect to a blood pressure can also be approximated to the Expression (6), the Expression (7) obtained on an assumption that the Expression (5) is the same as the Expression (6) can be assumed to be established between the blood pressure P and pulse wave amplitude J at any position irrespective of the height measuring position.

[Expression 6]

$$\frac{dI}{dP} \approx \frac{I_S - I_D}{P_S - P_D} = \frac{J}{D} \tag{6}$$

[Expression 7]

$$P \approx \frac{KD}{J} + \alpha \tag{7}$$

<Relationship between Systolic Blood Pressure $P_S$ and Pulse Wave Amplitude J>

On the other hand, when the pulse pressure $D = P_S - P_D$ is transformed and substituted into the Expression (3), Expressions (8) and (9) are obtained.

[Expression 8]

$$\frac{P_S - \alpha}{\gamma} = e^{I_S/K} \tag{8}$$

[Expression 9]

$$\frac{P_D - \alpha}{\gamma} = \frac{P_S - D - \alpha}{\gamma} = e^{I_D/K} \tag{9}$$

Dividing Expression (9) by Expression (8) by using the difference between the systolic (maximum value) and the diastolic (minimum value) of the pulse wave signals, that is, the pulse wave amplitude $J = I_S - I_D$ obtains Expression (10).

[Expression 10]

$$\frac{P_S - D - \alpha}{P_S - \alpha} = e^{-(I_S - I_D)/K} = e^{-J/K} \tag{10}$$

Expression (10) is transformed into Expression (11).

[Expression 11]

$$D + \alpha = P_S - (P_S - \alpha)e^{-\frac{J}{K}} \tag{11}$$

Here, since the amount of the change in the cross-sectional area of the vessel is minute, assuming that the last term in the right-hand member of Expression (11) can be approximated to Expression (12), Expression (13) can be obtained from the Expression (12).

[Expression 12]

$$e^{-\frac{J}{K}} \approx 1 - \frac{J}{K} \tag{12}$$

[Expression 13]

$$D = (P_S - \alpha)\frac{J}{K} \tag{13}$$

The Expression (13) does not also depend on the position, and is established between the systolic blood pressure $P_S$ at any position and the pulse wave amplitude J measured at that position.

From the above Expressions (7) and (13), it can be seen that a blood pressure P and a pulse wave amplitude J have a certain relationship therebetween. However, the value of J can be detected from the video signal, but the values K and D are unknowns.

Therefore, a case where measuring positions have a height difference is considered. For simplification, the expression is developed for systolic. Dividing the Expression (13) according to a higher position and a lower position and distinguishing by adding subscripts H and L, respectively, establish Expressions (14) and (15).

[Expression 14]

$$D_H = (P_{SH} - \alpha)\frac{J_H}{K} \tag{14}$$

[Expression 15]

$$D_l = (P_{Sl} - \alpha)\frac{J_L}{K} \tag{15}$$

At this time, assuming that the pulse pressure is unchanged in the both cases of the higher and lower positions, that is, a relationship $D_H = D_L$ is established because the Expression (14) and (15) are equal and therefore regarded to be Expression (16), and D and K are erased.

[Expression 16]

$$(P_{SH} - \alpha)J_H = (P_{SL} - \alpha)J_L \tag{16}$$

Expressing a difference between the local systolic blood pressure of a hand at the lower and higher positions by Expression (17) and transforming the Expression (16) gives Expression (18).

[Expression 17]

$$\Delta P = P_{SL} - P_{SH} \qquad (17)$$

[Expression 18]

$$(P_{SL} - \Delta P - \alpha)J_H = (P_{SL} - \alpha)J_L \qquad (18)$$

Further, when Expression (18) is transformed using Expression (19), Expression (20) is obtained.

[Expression 19]

$$R = \frac{J_L}{J_H} \qquad (19)$$

[Expression 20]

$$P_{SL} = \frac{\Delta P}{1 - R} + \alpha \qquad (20)$$

In Expression (20), the ratio information $R=J_L/J_H$ of the amplitude of a pulse wave signal (the difference between the maximum value and the minimum value in the beat) at the lower position to that of the higher position can be measured directly. This means that, if the values of the difference $\Delta P$ between the local systolic blood pressures at the higher position and the lower position and the coefficient $\alpha$ are known in addition to the value of R, the absolute value $P_{SL}$ [mmHg] of the systolic blood pressure at the lower position can be calculated from Expression (20).

If the vertical distance can be grasped, the value $\Delta P$, which is the pressure gradient between the higher and lower positions, can be considered to be close to the corresponding pressure of the water column (0.735 mmHg/cm) for the distance because the density of the blood is almost equal to that of water. Therefore, Expression 21 can be established when q=0.735 [mmHg/cm] and the vertical distance is h [cm], Expression (20) can be normalized to Expression (22).

[Expression 21]

$$\Delta P = qh \qquad (21)$$

[Expression 22]

$$P_{SL} = \frac{qh}{1 - R} + \alpha \qquad (22)$$

Hereinafter, Expression (22) is referred to as a blood pressure function. That is, this blood pressure function is derived from the above basic function, and can be said to be a function which includes compared value information (amplitude ratio information) as a variable and further includes a bias coefficient $\alpha$.

The diastolic blood pressure $P_{DL}$ at the lower position, the systolic blood pressure $P_{SH}$ at the higher position, and the diastolic blood pressure $P_{DH}$ at the higher position can be derived in the same manner by using the above Expressions (14)-(22). In addition, the vertical distance h can be estimated only from a video on the basis of the length of, for example, the hand or face in the video.

In addition, the calculation uses the density of water, as the term q, but the precision increases when the calculation uses the density of blood. A method for further improving the precision will be described below.

Figure 5:
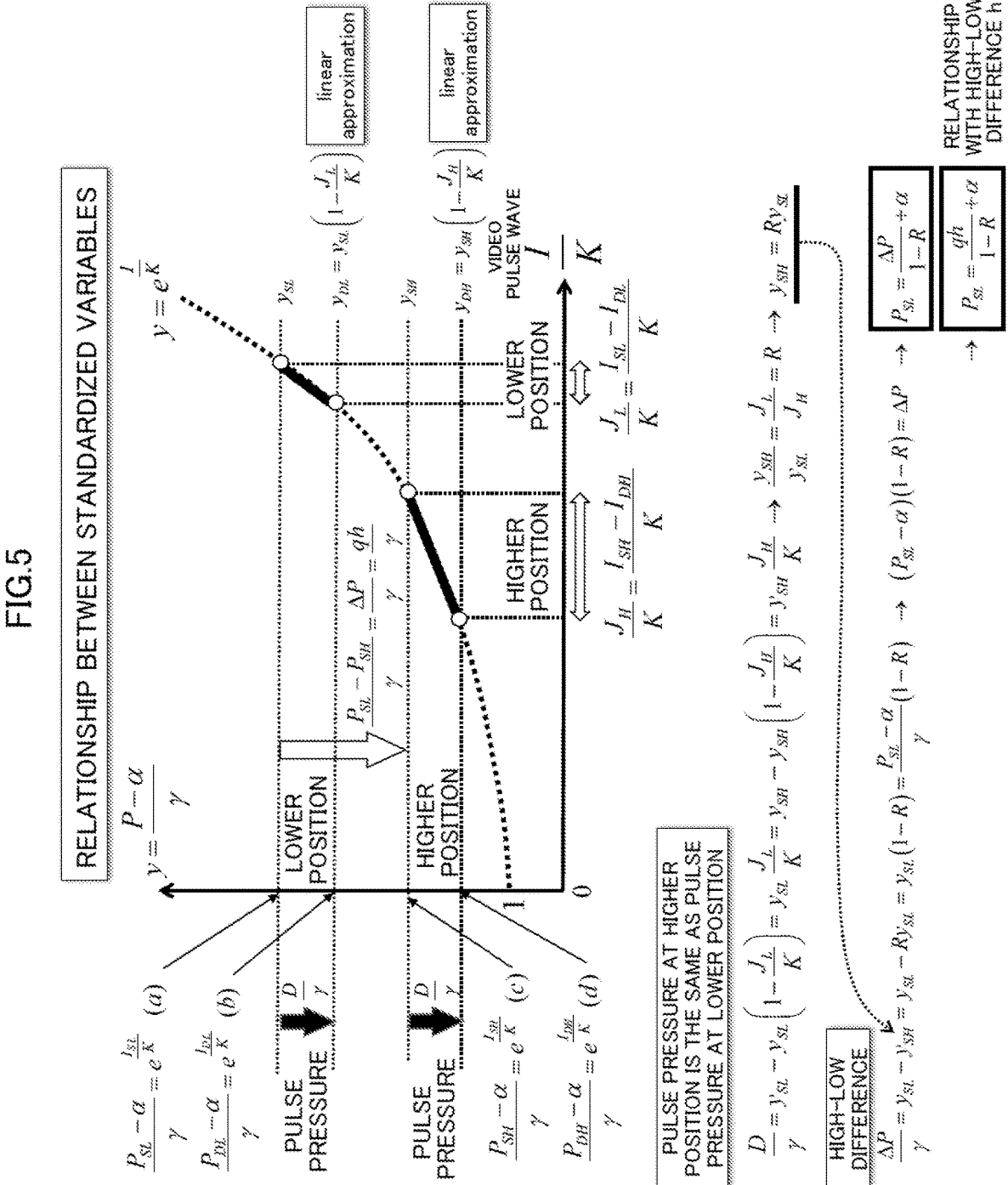
FIG. 5 is a diagram illustrating the embodiment.

FIG. 5 is a diagram illustrating a relationship of Expression (22). When attention is paid to the inclination of a straight line obtained linearly approximating a curve, the inclination is gentler at the higher position than at the lower position. This is caused by changes in the elasticity of the blood vessel relative to the intravascular pressure.

As described above, by using the amplitudes of the pulse wave signals at the higher and lower positions, the absolute value $P_{SL}$ [mmHg] of the low systolic blood pressure can be calculated in a few steps on the basis of the ratio information $R=J_L/J_H$ of the amplitude of a video pulse wave signal (the difference between the maximum value and the minimum value within a beat), which can be directly measured, at the lower position to that at the higher position, a difference $\Delta P=qh$ of the local systolic blood pressure at the higher and lower positions, and the bias coefficient $\alpha$. In other words, by directly substituting the value detected from the video signals into the Expression (22), it is possible to easily estimate the absolute value blood pressure P having the original unit [mmHg] of the measured amount without applying the regression expression.

The blood pressure estimating device 1 according to the embodiment estimates, upon on the above principle, the blood pressure on the basis of the ratio information $R=J_L/J_H$ of the pulse wave amplitude of the signal value (video pulse wave signal) representing the temporal change of the brightness value of the video signal at the lower position to that of the higher position and the height difference h. Hereinafter, for the processing by the blood pressure estimating device 1, description will now be made in relation to a process of detecting a measuring position from a video signal, a process of detecting pulse wave information from a video signal, and a process of estimating a blood pressure from the detected pulse wave information, detailing the respective element of the blood pressure estimating device 1.

3. FUNCTIONAL CONFIGURATION

Figure 2:
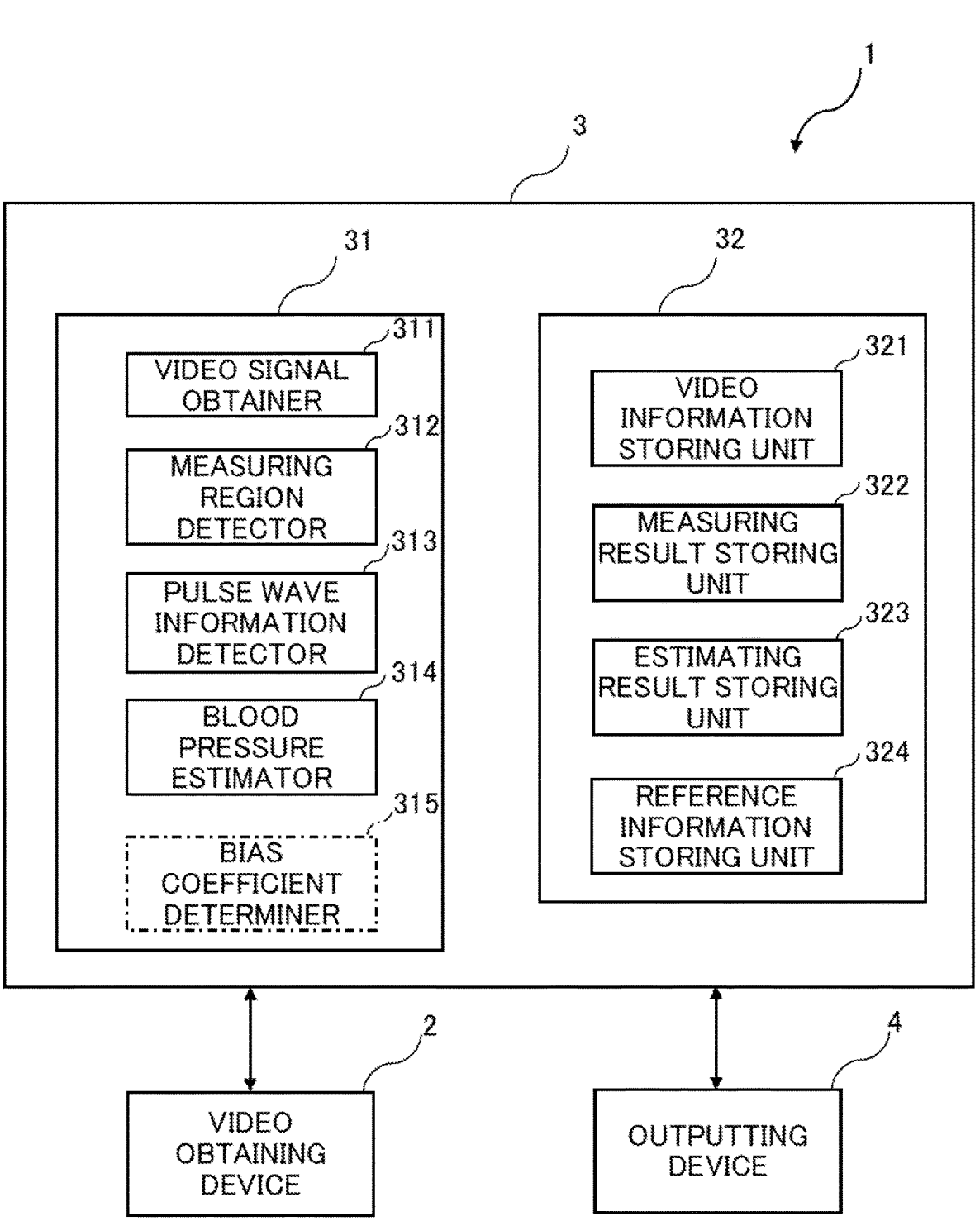
FIG. 2 is a block diagram illustrating a functional configuration of the apparatus for estimating a blood pressure according to the embodiment.

Description will now be made in relation to an example of the functional configuration of the blood pressure estimating device 1 according to the one embodiment with reference to FIG. 2. In the example of FIG. 2, some devices, cables, and the like in the information processing device 3 illustrated in FIG. 1 are omitted. As illustrated in FIG. 2, the function of the blood pressure estimating device 1 is mainly achieved by the information processing device 3. Furthermore, the information processing device 3 functionally includes a processing unit 31 and a storing unit 32.

[3-1. Processing Unit]

The processing unit 31 detects a distance between higher and lower measuring position in vertical direction (the measuring position at the higher position of the subject corresponds to the first position or the second position of the living body and the measuring position at the lower position of the subject corresponds to the second position or the first position of the living body) of the subject from video information (video signals) of the predetermined regions of the subject, detects video pulse wave signals (pulse wave information) at respective regions, and estimates the blood pressure on the basis of compared value information of the pulse wave amplitudes of the detected respective video pulse wave signal (when the video pulse wave signal at the higher measuring position corresponds to the first pulse wave information at the first position of the living body, the video pulse wave signal at the lower measuring position corresponds to the second pulse wave information at the second position of the living body, and when the video pulse wave signal at the higher measuring position corresponds to the second pulse wave information at the second position of the living body, the video pulse wave signal at the lower measuring position corresponds to the first pulse wave information at the first position of the living body).

[3-2. Respective Function of Processing Unit]

The processing unit 31 is a functional unit that is arithmetically processed by the CPU 3A, and each function thereof is configured as an individual program. As illustrated in FIG. 2, the processing unit 31 includes a video signal obtainer 311, a measuring region detector 312, a pulse wave information detector 313, and a blood pressure estimator 314.

<Video Signal Obtainer>

The video signal obtainer 311 obtains a video signal indicating a video of a predetermined part of the body of the subject via the video obtaining device 2. The video signal obtainer 311 outputs the obtained video signal of the subject to the measuring region detector 312 and the pulse wave information detector 313. The video signal obtainer 311 may obtain a video signal by reading a video signal information stored in a video information storing unit 321 of the storing unit 32 that is to be described below. The video signal obtainer 311 may obtain a video signal by receiving data containing a video signal which signal is stored in an external communication terminal or an external storing device via a network, an electric line, or the like.

<Measuring Region Detector>

The measuring region detector 312 detects a region of predetermined parts of the subject included in the video of a video signal obtained by the video obtaining device 2. The embodiment detects a face region, a palm region, a foot or foot sole region, and according to the requirement, the heart region (reference position). Examples of a method of detecting each measuring part includes a method by pattern matching, a method using a discriminator obtained by learning using a large number of sample videos of a face or a hand of a person. Alternatively, the face of the subject may be registered in a Read Only Memory (ROM) in advance, and the specific face may be recognized by performing face recognition after the detection of the subject. In addition, the heart region may be recognized to be a region within a certain range from the face region.

Further, the measuring region detector 312 also detects a skin region at each specific part. When the skin region is automatically extracted based on the color information in a video, the skin region of the subject can be extracted by extracting a region indicating the color of the skin from the video. More specifically, the measuring region detector 312 extracts all coordinates (coordinates of pixels) indicating a color (brightness value) corresponding to the skin color in the two-dimensional coordinate system of the video, and extracts a region of an aggregation of pixels having consecutive coordinates in the extracted coordinates as a skin region. As described above, the measuring region detector 312 can extract a skin region corresponding to each specific part of a body of a subject by extracting a region of an aggregation of pixels having consecutive coordinates.

The measuring region detector 312 may perform a tracking process regarding the specific part as the tracking-target region. As an example of the one embodiment, when two positions of a higher position and a lower position are generated by the passage of time using only one hand, such tracking process is performed when moving the one hand from a lower position (first position) to a higher position (second position). The tracking process retrieves, for example, a region (this region is the tracking region in the original frame image) in which the similarity between the feature value of the video in a tracking region in the previous frame image and the feature value of the video in the tracking candidate region of the current frame image is the highest from the current frame image.

The measuring region detector 312 executes the above detecting process on each frame constituting the video, and sequentially transmits the coordinates of the region in each frame to the pulse wave information detector 313.

The predetermined parts may be any parts as far as the parts have a difference in the vertical position therebetween. For example, the predetermined positions are appropriately selected from a hand placed near the heart and the face, the forehead and the jaw of the face, the right and left hands with a height difference, the soles of the right and left feet.

One of the predetermined parts may be moved to a higher position or a lower position during the measurement. Alternatively, as the predetermined parts, the measurement may be performed under a state where the both hands are placed at the same height position and then one of the hands is fixed at that position but the other hand is moved in the vertical direction.

Further alternatively, when, for example, a face is selected as a predetermined part, a predetermined part of the face may be measured in a sitting state at first, and then the face may be moved vertically by standing, and the predetermined part may be performed.

In the present embodiment, palms of both hands are used for the palm parts and the left hand is set to the lower position (L: first position) and the right hand is set to the higher position (H: second position). Defining the both palm parts as the predetermined parts is preferable because it is highly possible that the intrinsic elements of the blood vessel from the heart to the predetermined parts are substantially the same, so that the influence of the intrinsic properties of the blood vessel is small, and high measurement accuracy can be expected.

<Pulse Wave Information Detector>

The pulse wave information detector (the first pulse wave information detector and the second pulse wave information detector) 313 detects the video pulse wave signal representing a temporal change of the brightness value for each measuring position from the video signal in the skin region of the specific part of the subject, which video signal is detected by the measuring region detector 312. In the embodiment, the video pulse wave signal (the first pulse wave information) is detected from the video signal obtained at a lower position and the video pulse wave signal (the second pulse wave information) is detected from the video signal acquired at a higher position. The pulse wave information detector 313 outputs the detected pulse wave information signals (pulse wave information) to the blood pressure estimator 314.

As one example of detecting the brightness value of green light commonly used in video pulse waves, the pulse wave information detector 313 detects the brightness value of green light by applying a green filter to the skin region of each frame of the video, or by using the brightness value of "G (green color)". Then, the pulse wave information detector 313 detects the video pulse wave in a temporal change curve by calculating the average value of the brightness value of the green light for each frame. The pulse wave information detector 313 may perform smoothing of the video and remove artificial impulsive noise generated in the camera itself as the video obtaining device 2 before detecting the brightness value of the green light from the video signal. Incidentally, when the infrared light is used, the obtained brightness value of the infrared light can be used without being processed.

Figure 6:
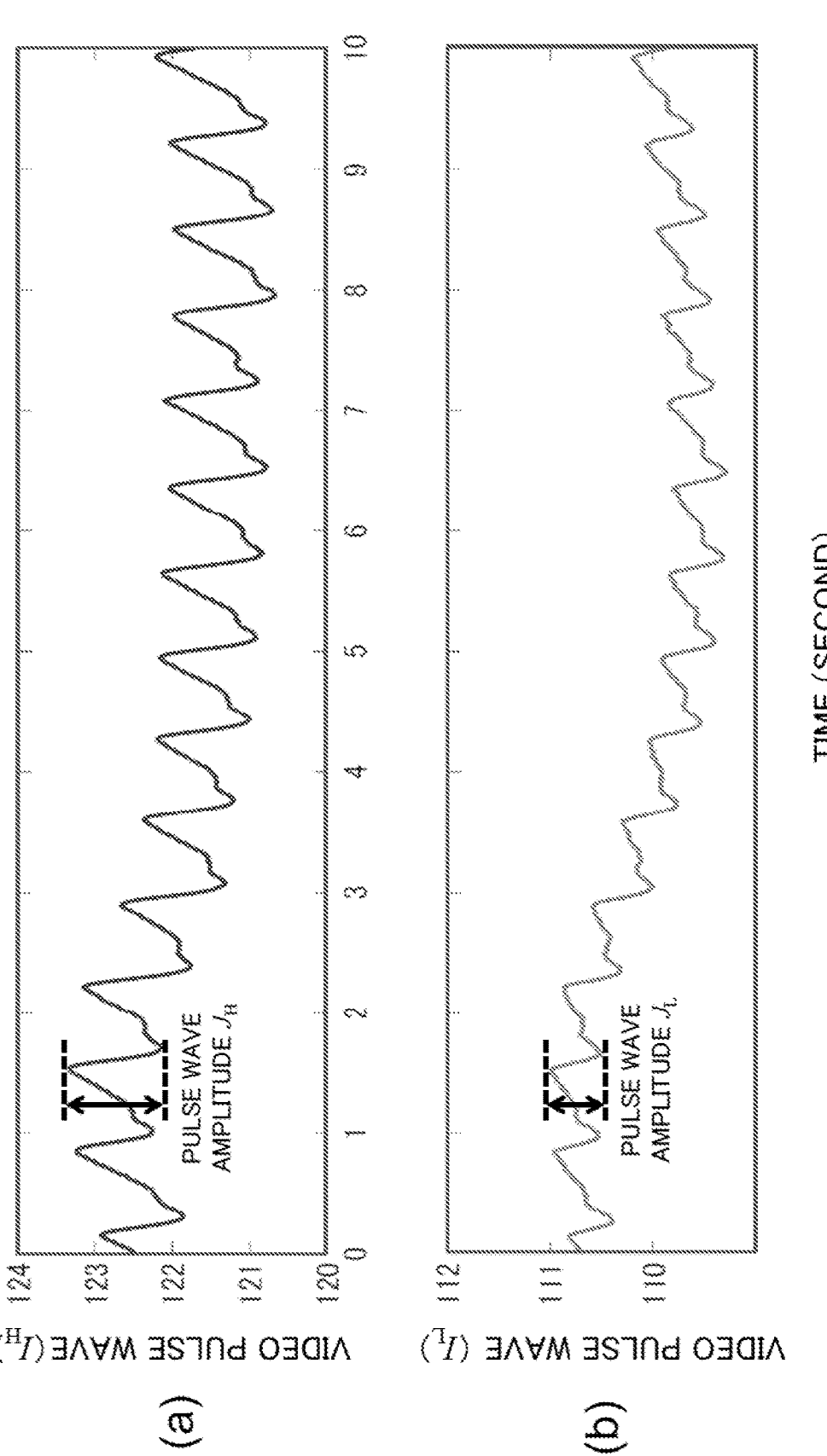
FIG. 6 is a diagram illustrating a pulse wave signal obtained in the present disclosure, (a) illustrating a pulse wave signal obtained at a higher position and (b) illustrating a pulse wave signal obtained at a lower position.

The video pulse wave signal detected in the present embodiment are shown in FIGS. 6(*a*) and 6(*b*). FIG. 6(*a*) shows the video pulse wave signal $I_H$ of the palm region at a higher position, and FIG. 6(*b*) shows the video pulse wave signal $I_L$ of the palm region at a lower position. As can be seen from FIGS. 6(*a*) and 6(*b*), there is a significant difference between video pulse wave signal $I_H$ at the higher position and video pulse wave signal $I_L$ at the lower position, which difference is specifically that the pulse wave amplitude $J_H$ at the higher position is larger than the pulse wave amplitude $J_L$ at the lower position.

<Blood Pressure Estimator>

The blood pressure estimator 314 estimates the absolute value of the blood pressure P using the Expression (22). The embodiment needs to obtain the difference h in the vertical direction, the ratio R of the pulse wave amplitude of the lower position to that of the higher position, and the bias coefficient α. The difference in the vertical direction may be determined in advance by defining a difference $h_V$ in the vertical direction beforehand or may be obtained from a video. As an example of obtaining the difference h from the video, the blood pressure estimator 314 calculates the size $h_F$ of the face region based on the coordinate of the measuring region inputted from the measuring region detector 312, and calculates the vertical difference (distance $h_V$) between the points of the center of gravity of the higher position and that of the lower position based on this size. The ratio of the pulse wave amplitude of the lower position to that of the higher position is obtained by calculating the pulse wave amplitudes $J_L$, $J_H$ from the pulse wave information (first pulse wave information and second pulse wave information) at the lower and higher positions input from the pulse wave information detector 313, and calculating the ratio (amplitude ratio information) R that is the compared value information of the amplitude of the video pulse wave signal of the palm at the lower position to the amplitude of the video pulse wave signal of the palm at the higher position.

The ratio R may be calculated by cutting out video pulse wave signals at the higher position and the lower position for each beat, obtaining the difference between the maximum value and the minimum value in the beat, and calculating the ratio of the difference of the lower position to the difference of the higher position. However, since the video pulse wave contains much noise, the ratio R may alternatively be calculated by obtaining the power spectra of the video pulse wave signals at the higher and lower positions in time series, obtaining the square roots of the largest frequency component in the range of frequencies related to the pulse wave, and obtaining the ratio of the obtained square roots.

The bias coefficient α is a literature value as shown in Table 1 or obtained through measurement on the subject with a cuff-type sphygmomanometer or the like, and is obtained from the storing unit 32, which will be described below.

The blood pressure estimator 314 estimates the absolute value of the blood pressure by substituting the difference h in the vertical direction, the ratio R of the pulse wave amplitude at the lower position to that at the higher position, and the bias coefficient α, which are calculated and obtained as described above, into the Expression (22).

[3-3. Storing Unit]

The storing unit 32 stores various types of data by means of a file system or a database system using a memory 3B. The storing unit 32 stores in advance programs that cause the CPU 3A to function the respective functional elements of the processor 31. These programs are collectively referred to as the program of the present disclosure (the aforementioned a program for estimating a blood pressure). The storing unit 32 may be a storing device 3C shown in FIG. 1.

[3-4. Respective Functions of Storing Unit]

As shown in FIG. 2, the storing unit 32 includes the video information storing unit 321, a measuring result storing unit 322, an estimating result storing unit 323, and a reference information storing unit 324.

<Video Information Storing Unit>

The video information storing unit 321 stores video signals. Specifically, the video information storing unit 321 stores video signals of a subject obtained by the video obtaining device 2. For example, the video information storing unit 321 stores video signals indicating a video including a predetermined part of the subject. The video information storing unit 321 stores a video signal and the temporal information of the time of taking a video of the subject in association with each other.

<Measuring Result Storing Unit>

The measuring result storing unit 322 stores the size $h_F$ of the face region calculated by the blood pressure estimator 314, the vertical distance by of the points of centers of gravity of the palm regions at the higher and lower positions, the pulse wave amplitudes $J_L$, and $J_H$ of the pulse wave information signals, and the ratio (amplitude ratio information) R which is the compared value information of the pulse wave amplitude at the lower position with respect to that at the higher position. At this time, the measuring result storing unit 322 stores the measuring information that associates the date and time of the estimation with the measuring result for each subject. If the vertical distance $h_V$ is known in advance, the size $h_F$ of the face region may be omitted.

<Estimating Result Storing Unit>

The estimating result storing unit 323 stores an estimated blood pressure value estimated by the blood pressure estimator 314. At this time, the estimating result storing unit 323 stores measurement information in which the estimated date and time and the measurement result are associated with each other for each subject.

<Reference Information Storing Unit>

The reference information storing unit 324 stores the bias coefficient α and the water column pressure q serving as the reference information referred to by the blood pressure estimator 314 in the estimation process. The reference information may be literature values, or may be updated by the subject periodically measuring with a cuff-type sphygmomanometer or the like.

4. FLOW DIAGRAM

Figure 3:
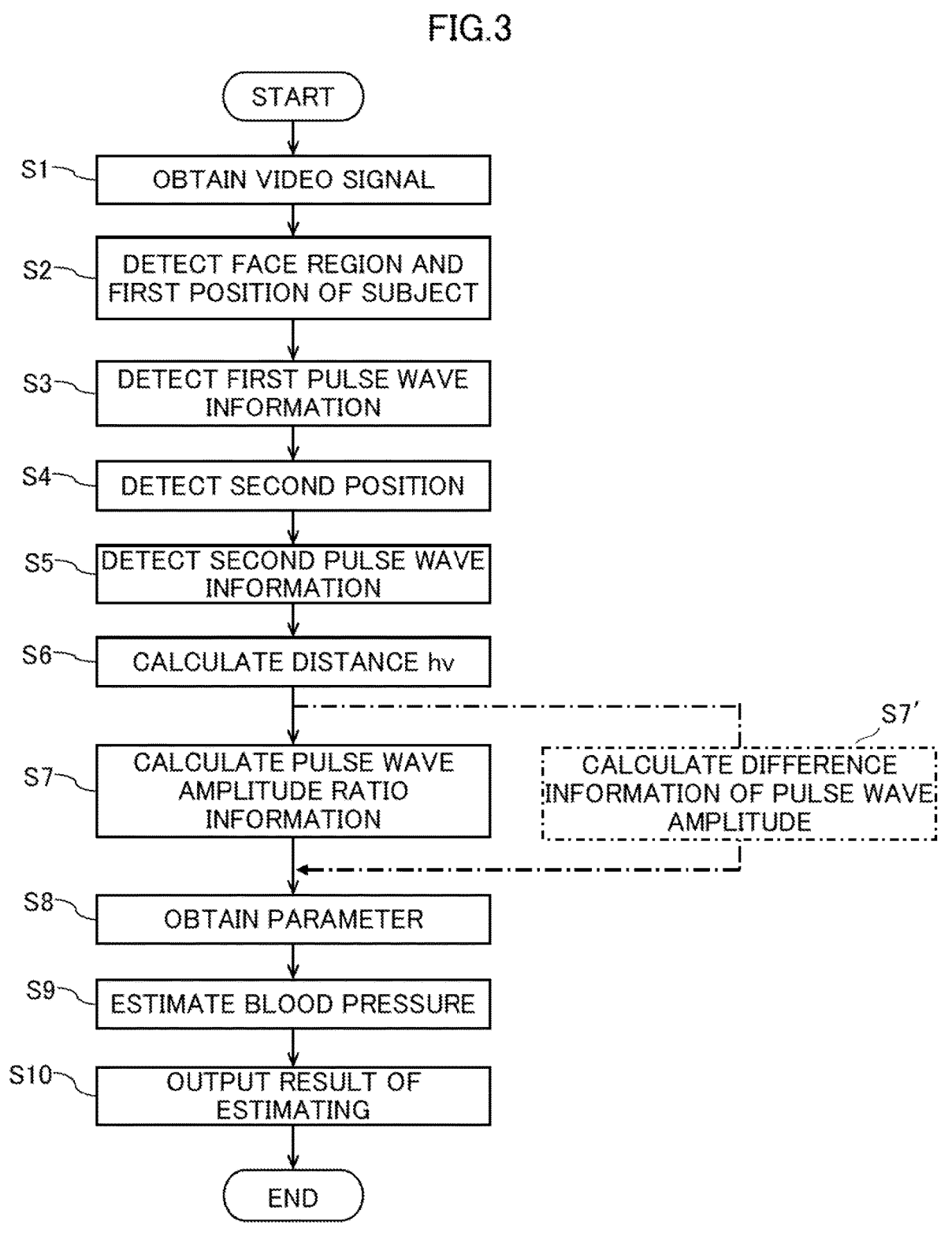

FIG. 3 is a flow diagram illustrating the contents of the above-described processing performed in the blood pressure estimating device 1.

First, the video obtaining device 2 takes a video of the subject to obtain the video signal, and the obtained video signal is input into the video signal obtainer 311 of the information processing device 3 (Step S1).

Next, the measuring region detector 312 of the information processing device 3 receives the video signal obtained in Step S1 from the video signal obtainer 311, and detects, for example, the face region, the palm region at the lower position, the sole of the foot (first position) of the subject (Step S2). Subsequently, the pulse wave information detector 313 receives the video signal obtained in Step S1 and the first position information detected in Step S2, and detects a video pulse wave signal (first pulse wave information) at the first position on the basis of the received signal and information (Step S3).

Similarly, the measuring region detector 312 of the information processing device 3 detects the palm region at the high position or the foot sole (second position) of the subject from the video signal obtained in Step S1 (Step S4). Subsequently, the pulse wave information detector 313 of the information processing device 3 receives the video signal obtained in Step S1 and the second position information detected by the measuring region detector 312 in Step S4, and detects the video pulse wave signal (second pulse wave information) at the second position based on received signal and information (Step S5).

Subsequently, the blood pressure estimator 314 of the information processing device 3 calculates the distance $h_V$ between the two positions based on the first position information and the second position information detected in Steps S2 and S4, respectively (Step S6). Incidentally, if the distance $h_V$ of the vertical direction is known in advance, the blood pressure estimator 314 may read the distance $h_V$ information from the storing unit 32 that stores the distance $h_V$ information. Subsequently, the blood pressure estimator 314 calculates the compared value information (amplitude ratio information) of the pulse wave amplitude based on the first pulse wave information and the second pulse wave information detected in Steps S3 and S5, respectively (Step S7).

Further, the blood pressure estimator 314 of the information processing device 3 obtains the necessary parameters q and a from the reference information storing unit 324 (Step S8) and estimates the blood pressure based on the Expression (22) (Step S9). The blood pressure estimator 314 outputs the estimating result to the estimating result storing unit 323 and the outputting device 4 (Step S10).

The processing of Steps S2 to S5 may be performed in the order from the higher position to the lower position, and the order of the respective steps may be reversed or may be performed simultaneously.

5. RESULT OF THE PRESENT EMBODIMENT

Using the blood pressure estimating device 1 of the present embodiment, the left hand is set to the low position (L: first position) and the right hand to the higher position (H: second position), the video obtaining device 2 took a video, and the processing unit 31 estimated the absolute value of the blood pressure P on the basis of the Expression (22).

Simultaneously with obtaining the blood pressure P in terms of the video pulse wave by taking a video, the blood pressure was measured using a continuous sphygmomanometer (Finometer Midi; Finapres Medical Systems) as a true value for comparing the precision of the blood pressure, and the two blood pressure values were compared.

The measurement was carried out for 60 seconds, and in the course of the measurement, the subject made foot pedaling operation with an Aerobike® in order to give a blood pressure variation. The video pulse wave signals obtained under cases of the left hand at a lower position and the right hand at a higher position are shown in FIGS. 6(a) and 6(b).

The height differences of the right and left hands were h=50 cm, and the bias coefficient $\alpha$ of $\alpha$=40 mm Hg, which was the literature value in Table 1, and q=0.735 [mmHg/cm] (density of blood=density of water) was used. The result of estimating the blood pressure P on the basis the Expression (22) are shown in Table 2 as the correlation coefficient and the root mean square error (RMSE) between the estimated blood pressure P and the blood pressure (hereinafter referred to as the true blood pressure) measured with the continuous sphygmomanometer.

TABLE 2

| Correlation and error of blood pressure (result of estimating systolic blood pressure at lower position) | | |
|---|---|---|
| | Correlation Coefficient | RMSE [mmHg] |
| Subject 1 | 0.57 | 31.7 |
| Subject 2 | 0.61 | 54.6 |
| Subject 3 | 0.53 | 51.2 |
| Subject 4 | 0.89 | 7.15 |
| Subject 5 | 0.61 | 68.8 |

Although the estimated blood pressures were relatively highly correlated with the actually measured values, the magnitude of the RMSE largely varied with subjects.

The present embodiment used a literature value as the bias coefficient $\alpha$, but it is considered that the bias coefficient $\alpha$ changes with an individual difference and the status of the subject. When the bias coefficient $\alpha$ was appropriately changed in each subject, RMSE was improved as compared with Table 2, respectively, and the best values of the RMSE of many subjects were less than 10 mmHg.

From the above, it is verified that the blood pressure estimating device 1 of the present embodiment can estimate the blood pressure, and if the value of the bias coefficient $\alpha$ is accurately obtained, there is a possibility that the blood pressure can be estimated with high accuracy.

6. ACTIONS AND EFFECTS

As described above, the blood pressure estimating device 1 according to the embodiment can easily estimate the blood pressure based on the measuring positions of the higher and lower positions of the specific parts of the subject that the measuring region detector 312 detects from the video signals calculated or detected by the video obtaining device 2, and the ratio information of the pulse wave amplitude of the pulse wave information of the higher and lower positions detected by the pulse wave information detector 313. Further, since the blood pressure estimating device 1 of the embodiment does not require any information related to the time such as a phase difference, the blood pressure estimation is directly performed without applying the regression expression to values that can be detected only from a video signal, so that the blood pressure can be estimated in fewer steps.

In the above blood pressure estimation, the video pulse wave is used for the pulse wave measurement, but since the Expression (22) can estimate a blood pressure P only if pulse wave signals of the higher and lower positions of a living body, not being limited to signals obtained from the video, the blood pressure can also be estimated by measuring predetermined positions having a difference in height by a device that detects a pulse wave such as a photoelectric pulse wave meter.

7. MODIFICATIONS

[7-1. Modification to Blood Pressure Estimation]

The foregoing embodiment illustratively describes the case where the blood pressure is estimated on the basis of the pulse wave amplitude ratio information of the video pulse wave signal, but the blood pressure may be estimated on the basis of the difference information of the pulse wave amplitudes of the video pulse wave signals.

Considering the Expression (7) for the lower position (L) and the higher position (H), the systolic blood pressure $P_{SL}$ at the lower position (L) is expressed by following Expression (23).

[Expression 23]

$$P_{SL} \approx \frac{KD}{J_L} + \alpha \qquad (23)$$

The systolic blood pressure $P_{SH}$ at the higher position (H) is expressed by following Expression (24).

[Expression 24]

$$P_{SH} \approx \frac{KD}{J_H} + \alpha \qquad (24)$$

Further, subtracting the Expression (24) from the Expression (23) obtains the Expression (25), so that the Expression (26) is obtained.

[Expression 25]

$$P_{SL} - P_{SH} = \Delta P \approx KD\left(J_L^{-1} - J_H^{-1}\right) \qquad (25)$$

[Expression 26]

$$KD \approx \frac{\Delta P}{J_L^{-1} - J_H^{-1}} \qquad (26)$$

Substituting the Expression (26) into the Expression (23) results in the Expression (27),

[Expression 27]

$$P_{SL} \approx \frac{\dfrac{\Delta P}{J_L^{-1} - J_H^{-1}}}{J_L} + \alpha \qquad (27)$$

which can be transformed into Expression (28) when the

Expression (19)

$$R = \frac{J_L}{J_H}$$

is applied. The Expression (28) results in the same as the Expression (20).

[Expression 28]

$$P_{SL} \approx \frac{\Delta P}{1 - R} + \alpha \qquad (28)$$

Assuming that $\Delta P = qh$ is established, substituting $\Delta P = qh$ into the Expression (26) gives the Expression (29).

[Expression 29]

$$KD = \frac{qh}{J_L^{-1} - J_H^{-1}} \qquad (29)$$

Since the right side of the Expression (29) can be actually measured, the term KD comes to be a known value. When the value KD is expressed by G=KD, the Expression (7) gives the Expression (30).

[Expression 30]

$$P \approx \frac{G}{J} + \alpha \qquad (30)$$

The term G of the Expression (30) represents the difference information of the pulse wave amplitudes J of the video pulse wave signals, and can be directly measured. Hereinafter, the Expression (30) is also referred to as a blood pressure function. That is, this blood pressure function is derived from the above basic function, and can be said to be a function which uses the compared value information (difference information) as a variable and further includes the bias coefficient $\alpha$.

The above process of the modification corresponds to the process (Step S7') of calculating the difference information in the flow diagram of FIG. 3. Also in the method that uses the difference information, the process of Steps S2 to S5 may be performed in the order from the higher position to the lower position, and the order of the respective steps may be reversed or may be performed simultaneously.

[7-2. Modification that Uses Variation Parameter Map]

The foregoing embodiment and the modification estimate the blood pressure by calculation based on the Expressions (22) and (30), but alternatively, the blood pressure may be estimated using information stored in advance in the storing unit 32. In this case, when the hand is fixed so that the height difference h of the detecting positions is a predetermined position, for example, the term qh in the Expression (22) is a constant value and as shown in FIG. 7, the value P' of qh/(1−R) calculated in combination of the constant value qh and multiple patterns R is stored as the map M1 in the reference information storing unit 324 and also the bias coefficient $\alpha$ corresponding to the subject is stored as the map M2 in the reference information storing unit 324. In this case, when the value R is detected from a pulse wave signal, values P' and $\alpha$ corresponding to the detected R may be read, and the blood pressure may be estimated on the basis of a simple arithmetic expression P=P'+$\alpha$.

Similarly, the combination of J and G=KD is stored as the map M1' in the storing unit 32, and the bias coefficient $\alpha$ corresponding to the subject is stored as the map M2. In this case, when the value J is detected from a pulse wave signal, values P" and $\alpha$ corresponding to the detected J may be read, and the blood pressure may be estimated on the basis of a simple arithmetic expression P=P"+$\alpha$. In addition, similarly, multiple maps may be prepared for different a.

[7-3. Modification of Bias Coefficient]

The foregoing embodiment uses the literature value 43 to 53 mmHg shown in Table 1 as the bias coefficient $\alpha$, but the bias coefficient $\alpha$ seems to be changed with individuals and the circumstance as described above. Therefore, a method of correcting $\alpha$ will be described below.

First, the true value $P_0$ of the blood pressure is measured by a sphygmomanometer with the hand adjusted to a position equal to the height of the heart (reference position). A pulse wave amplitude $J_0$ is measured from the video at that time. Assigning $P_0$ and $J_0$ into the Expression (30) with $\alpha$ as an unknown number obtains the Expression (31).

[Expression 31]

$$\alpha = P_0 - \frac{G}{J_0} \tag{31}$$

Assuming that $\alpha$ determined by the Expression (31) is $\alpha^*$, a blood pressure can be estimated as in the Expression (32).

[Expression 32]

$$P \approx \frac{G}{J} + \alpha \tag{32}$$

The estimation based on the Expression (32) requires only four values of the following i) to iv).

i) the value $J_L$ at a lower position measured from a video
  ii) the value $J_H$ at a higher position higher by h cm than the lower position measured by the video
  iii) the value $J_0$ at the position of the heart measured from the videos
  iv) the true value $P_0$ of the blood pressure corresponding to iii) measured with a sphygmomanometer When the Expression (22) is used, the pulse wave amplitudes $J_L$ and $J_H$ of the hand at two positions having a height difference of h cm must be calculated. On the other hand, in the method using the Expression (32), once G=KD is determined by substituting $J_L$ and $J_H$ into the Expression (29) and $\alpha'$ is determined by substituting $J_0$ and $P_0$ into the Expression (31), the blood pressure P can be more easily estimated from the pulse wave amplitude J using the Expression (32).

If $J_L$ is in the position of the heart, i.e. in the case of $J_0 = J_L$, a $J_0$ may be replaced with the $J_L$.

Further, since $\alpha^*$ may vary according to the state of the subject, it is desirable to periodically calculate and update the value of $\alpha^*$ stored in the reference information storing unit 324. The processing unit 31 further includes a bias coefficient determiner 315, and performs a process for determining the bias coefficient $\alpha^*$.

In the modification described above, the position of the heart measured from the video is detected by the measuring region detector 312. Further, the values measured for using the Expression (32), which specifically are $J_0$ at the position of the heart measured from the video and the true value $P_0$ of the blood pressure corresponding to $J_0$ and being the value measured with the sphygmomanometer are stored in the measuring result storing unit 322 for each subject. Further, the bias coefficient $\alpha^*$ calculated based on the Expression (32) is stored in the reference information storing unit 324 for each subject.

[7-4. Modification that Uses Accurate q for Each Individual]

The foregoing scheme uses the density of water as the value q used on the assumption that the density of blood is approximately equal to the density of water. However, the use of the blood density enhances the precision. Since it should be noted the density of the blood varies individually, the precision can be enhanced if the density of the blood for each individual can be easily obtained.

Hereinafter, a scheme of simply obtaining the density of blood will be described.

First, a predetermined part of the subject is placed at a low position, and the blood pressure $P_L$ of the predetermined part is measured. Next, in this condition, the predetermined part is raised to a higher position by the vertical distance h, and the blood pressure $P_H$ of the predetermined part is measured. The differences between the blood pressure $P_L$ at the lower position and the blood pressure $P_H$ the higher position are expressed by the Expression (33) with reference to Expressions (17) and (21).

[Expression 33]

$$\Delta P = qh = P_L - P_H \tag{33}$$

Applying the obtained local blood pressure $\Delta P$ to the Expression (22) makes it possible to use the value qh dedicated to each subject, so that a more precise blood pressure can be estimated.

For the blood pressure measurement at this time, any known sphygmomanometer such as a cuff-type sphygmomanometer or a continuous sphygmomanometer can be used. When a continuous sphygmomanometer is used, continuous blood pressure values at the lower position and at the higher position obtained during a predetermined time period may be used as average values, respectively, and may obtain a difference between the lower-position average blood pressure and the higher-position average blood pressure as the difference between the blood pressures at the lower position and at the lower position.

Further, as described in the above modification that uses a parameter map, mapping the relationship of the local blood pressure $\Delta P$ to multiple vertical distances h makes it possible to easily estimate a precise blood pressure.

[7-5. Modification of Calculating Parameter]

Here, a method of obtaining the unknown parameter of the Expression (30) by using a lot of data is also proposed. If the Expression (30) can be assumed to be always satisfied, it is further assumed that K ($\geq 2$) distinct blood pressure $P_K$ measured by the sphygmomanometer and pulse wave amplitudes $J_k$ (k=1, 2, . . . , K) are obtained by providing some blood pressure variation. At this time, the estimated values G (with hat) and $\alpha$ (with hat) of the unknown parameters of the Expression (32) can be obtained by the least squares method. That is, when the Expression (34) is set, G (with hat) and $\alpha$ (with hat) establish the Expression (37) serving as the solution of the normal Equation that minimizes the norm (Expression (36)) of the residuals of the model (Expression 35).

[Expression 34]

$$y = \begin{bmatrix} P_1 \\ P_k \\ \vdots \\ P_K \end{bmatrix}, A = \begin{bmatrix} 1 & J_1^{-1} \\ 1 & J_2^{-1} \\ \vdots & \vdots \\ 1 & J_K^{-1} \end{bmatrix}, x = \begin{bmatrix} \alpha \\ G \end{bmatrix} \tag{34}$$

[Expression 35]

$$y = Ax + \varepsilon \tag{35}$$

-continued

[Expression 36]

$$\varepsilon^T \varepsilon = (y - Ax)^T (y - Ax) \qquad (36)$$

[Expression 37]

$$\begin{bmatrix} \hat{\alpha} \\ \hat{G} \end{bmatrix} = (A^T A)^{-1} A^T y \qquad (37)$$

The minimum number of data required at this time is the following four pieces of data.

i) Two different pulse wave amplitudes $J_1$ and $J_2$ measured from the video ii) Two different blood pressures $P_1$, and $P_2$ measured by a sphygmomanometer However, it is necessary to provide some blood pressure variation so that the two blood pressures comes to be different from each other.

Further generalization of the Expression (30) on the assumption that the Expression (38) is established with respect to different blood pressure $P_k$ and pulse wave amplitudes $J_k$ (k=1, 2, . . . , K) seems to establish a model (Expression (39), most common multiple regression model) obtained by ordinarily extending the Expression (36) to the the n-th order (where n≤K).

[Expression 38]

$$P_k = a_0 + a_1 J_k^{-1} + a_2 J_k^{-2} + a_3 J_k^{-3} + \dots a_n J_k^{-n} + \varepsilon \qquad (38)$$

[Expression 39]

$$y = Ax + \varepsilon \qquad (39)$$

Here, Expression (40) is given.

[Expression 40]

$$y = \begin{bmatrix} P_1 \\ P_k \\ \vdots \\ P_K \end{bmatrix}, A = \begin{bmatrix} 1 & J_1^{-1} & J_1^{-2} & \dots & J_1^{-n} \\ 1 & J_2^{-1} & J_2^{-2} & \dots & J_2^{-n} \\ \vdots & \vdots & \vdots & \vdots & \vdots \\ 1 & J_K^{-1} & J_K^{-2} & \dots & J_K^{-n} \end{bmatrix}, x = \begin{bmatrix} a_0 \\ a_1 \\ \vdots \\ a_n \end{bmatrix} \qquad (40)$$

The estimating parameter is obtained as the Expression (41).

[Expression 41]

$$x = (A^T A)^{-1} A^T y \qquad (41)$$

The minimum number of data required at this time is the following 2n pieces of data.

i) the number n different pulse wave amplitudes $J_k$ (k=1, 2, . . . n) measured from the video ii) n different blood pressures $P_k$ (k=1, 2, . . . , n) measured by a sphygmomanometer The present modifications can obtain the same effect as that of the foregoing embodiment except that the values calculated are different.

[7-6. Modification that Uses Correction Coefficient for Each Part]

The method of the present disclosure can obtain the pulse wave amplitudes J having the equal value if measuring different predetermined parts of the living body at the same height. However, for example, when the right and left hands are placed at the same height position and the respective pulse wave amplitudes J are measured, it can be seen that the measured amplitudes are slightly different from each other.

It is considered that this difference is caused by the characteristics of the blood vessels of the right hand and the left hand not being completely the same. Naturally, even if the measurement is conducted at the same height, the pulse wave amplitudes J of parts, such as the hand and the face, obviously having different characteristic of the blood vessel characteristics are different from each other. If the pulse wave amplitude J is different with part, the estimation of the blood pressure is also influenced as a matter of course. Therefore, correction is required for each part.

Hereinafter, description will now be made in relation to a method of correcting each part in an example of a case of using the both hands, specifically, placing the right hand at the higher position and the left hand at the lower position.

Here, the pulse wave amplitudes $\Delta J_{left}$, $\Delta J_{right}$ of the right and left hands measured at the same height are assumed to be different from each other.

At this time, when a ratio (pulse wave amplitude ratio for each part) R of the left pulse wave amplitude to the right pulse wave amplitude $R_{LR}$ gives the Expression (42).

[Expression 42]

$$R_{LR} = \Delta J_{left} / \Delta J_{right} \qquad (42)$$

If $R_{LR}$ is a constant value, the original deviation (difference) between the right-hand pulse wave amplitude $\Delta J_{right}$ and the left-hand pulse wave amplitude $\Delta J_{left}$ can be corrected. The Expression (42) can be transformed into Expression (43).

[Expression 43]

$$\Delta J_{left} = R_{LR} \cdot \Delta J_{right} \qquad (43)$$

Accordingly, the blood-pressure estimating Expression excluding the effect of the difference between the left and right pulse wave amplitudes (difference for respective parts) can be obtained from the Expression (44) from the Expression (22), the ratio information $R=J_L/J_H$ of the lower position to the higher position, and the Expression (42).

[Expression 44]

$$P_{SL} = \frac{qh}{1 - \dfrac{J_L}{R_{LR} \cdot J_H}} + \alpha \qquad (44)$$

Therefore, it can be said that the ratio $R_{LR}$ is a correction coefficient for correcting the pulse wave information of the different parts.

As the above, the ratio of the left and right pulse wave amplitude (pulse wave amplitude ratio for each part) $R_{LR}$ can be easily measured.

When the right hand and the left hand are used as the specific parts, the ratio $R_{LR}$ is obtained by fixing both hands at the same height position and measuring the respective pulse wave amplitudes using a video pulse wave or a photoelectric pulse wave meter. To increase the precision of $R_{LR}$, this measurement can be carried out multiple times to obtain the average value of $R_{LR}$.

By correcting the pulse wave amplitude for each part using the ratio $R_{LR}$ of the pulse wave amplitude for each part that can be obtained easily, the blood pressure can be estimated more precisely. In addition, by associating multiple parts with respective corresponding ratios of the pulse wave amplitudes, it is possible to correct the pulse wave amplitude of a different part only by measuring one part, so that the load of measurement can be reduced.

8. MISCELLANEOUS

In the embodiment, the video capturing device are assumed to be a color video or a monochrome video, but that of the present disclosure is not limited thereto. As described above, since the signal value I of the video pulse wave and the blood vessel cross-sectional area A are proportional to each other, it is sufficient to obtain information in which this relationship is reflected. Therefore, the video capturing device may use an infrared video or may use ultrasonic waves.

In the foregoing embodiment, description is made in relation to a scheme of calculating the size $h_F$ of a face region and then calculating the difference (distance $h_V$) in the points of the center of the gravity in the vertical direction between the palm regions at the lower and higher positions. Alternatively, the size of another region except for the face and the difference (distance $h_V$) in the center of the gravity in the vertical direction of the tip of the longest finger other than the palms may be calculated. The basis for calculating the distance $h_V$ may be other than the living body.

In the embodiment, the blood pressure is estimated without using time-related information (pulse wave propagation velocity), such as phase information, but the use of the information is not precluded in order to enhance the accuracy. The blood pressure information obtained in the embodiment may be corrected using the blood pressure estimated by the pulse wave propagation speed, a parameter related to the pulse wave propagation speed, or the like. Conversely, the blood pressure estimated by the pulse wave propagation velocity may be corrected by the parameter or the blood pressure value of the embodiment.

In one aspect, according to the disclosed apparatus, method, and a non-transitory computer-readable recording medium having stored therein a program for estimating a blood pressure, by estimating a blood pressure of the living body on the basis of the compared value information (preferably, pulse wave amplitude information) between the first pulse wave information detected at the first position of the living body and the second pulse wave information detected at the second position which is distant in the vertical direction from the first position of the living body, it is possible to directly estimate the absolute value of the blood pressure from the pulse wave signal with fewer processing steps without requirement of obtaining a phase difference depending on time, and also possible to enhance the precision in estimation of a blood pressure.

In the claims, the indefinite article "a" or "an" does not exclude a plurality.

All examples and conditional language recited herein are intended for the pedagogical purposes of aiding the reader in understanding the disclosure and the concepts contributed by the inventor to further the art, and are not to be construed limitations to such specifically recited examples and conditions, nor does the organization of such examples in the specification relate to a showing of the superiority and inferiority of the disclosure. Although one or more embodiments of the present disclosures have been described in detail, it should be understood that the various changes, substitutions, and alterations could be made hereto without departing from the spirit and scope of the disclosure.

What is claimed is:

1. An apparatus for estimating a blood pressure comprising:

a video camera configured to obtain a video signal of a predetermined part of a body of a living body;

a memory;

a processor having processor circuitry coupled to the memory; and a display configured to display a video obtained by the video camera and information representing a result of processing performed by the processor circuitry in the processor, the processor circuitry in the processor comprising video signal obtaining processor circuitry, measuring region detector processor circuitry, video pulse wave signal detector processor circuitry, and blood pressure estimating processor circuitry, wherein the video signal obtaining processor circuitry obtains the video signal of the predetermined part of the body of the living body from the video camera, the measuring region detector processor circuitry specifies, from the video signal obtained by the video signal obtaining processor circuitry, a part of skin region from which video pulse wave signal in the predetermined part is obtained, the video pulse wave signal detector processor circuitry comprises:

first video pulse wave signal detector processor circuitry configured to detect first video pulse wave signal from the video signal obtained at a first position of the living body, the first position being included in the specified skin region, and second video pulse wave signal detector processor circuitry configured to detect second video pulse wave signal from the video signal obtained at a second position of the living body, the second position being included in the specified skin region and being spaced a distance in a vertical direction from the first position, and the blood pressure estimating processor circuitry estimates, based on first pulse wave amplitude, which is a difference between the maximum value and the minimum value within a beat, at the first position obtained from the first video pulse wave signal obtained by the first video pulse wave signal detector processor circuitry, second pulse wave amplitude, which is a difference between the maximum value and the minimum value within a beat, at the second position obtained from the second pulse wave signal obtained by the second pulse wave detector processor circuitry, and the distance between the first position and the second position in the vertical direction, the blood pressure of the living body, wherein the blood pressure estimating processor circuitry estimates the blood pressure of the living body using an expression $$P = gh/(1-R) + \alpha$$

where, q represents a density; h represents the distance in the vertical direction; R represents a ratio of the first pulse wave amplitude at the first position to the second pulse wave amplitude at the second position; and a represents a bias coefficient.

2. The apparatus according to claim 1, wherein the blood pressure estimating processor circuitry estimates the blood pressure of the living body by inputting a value calculated from the first pulse wave amplitude and the second pulse wave amplitude into the expression, the expression being a blood pressure function derived from a basic function and using the value as a variable and further including the bias coefficient, the bias coefficient being stored in the memory and depending on a characteristic of a blood vessel of the living body, and the basic function including the bias coefficient and representing a relationship between the blood pressure of the living body and a cross-section of the blood vessel of the living body.

3. The apparatus according to claim 2, further comprising bias coefficient determining processor circuitry configured to determine the bias coefficient based on the first pulse wave amplitude, the second pulse wave amplitude, a blood pressure measurement of the living body at a reference position of the living body and a pulse wave amplitude at the reference position of the living body.

4. The apparatus according to claim 1, wherein the blood pressure estimating processor circuitry estimates, based on the ratio of the first pulse wave amplitude to the second pulse wave amplitude and the distance between the first position and the second position in the vertical direction, the blood pressure of the living body.

5. The apparatus according to claim 1, wherein the first pulse wave amplitude is obtained at a predetermined region of the living body, and the second pulse wave amplitude is obtained at the predetermined region being moved.

6. The apparatus according to claim 1, wherein the first pulse wave amplitude is obtained at a first hand of the living body at the first position, and the second pulse wave amplitude is obtained at a second hand of the living body at the second position.

7. The apparatus according to claim 1, wherein the first pulse wave amplitude is obtained at a first hand of the living body at the first position, and the second pulse wave amplitude is obtained at a second hand of the living body, the second hand being moved to the second position.

8. The apparatus according to claim 1, wherein a correction coefficient is obtained from two pulse wave amplitudes obtained at two different predetermined regions of the living body, the predetermined regions being at a same level in the vertical direction, and at least one of the two pulse wave amplitudes is corrected by using the correction coefficient.

9. A method for estimating blood pressure in an apparatus for estimating a blood pressure comprising a video camera configured to obtain a video signal of a predetermined part of a body of a living body, the apparatus comprising:

a memory; a processor including processor circuitry coupled to the memory; and a display configured to display a video obtained by the video camera and information representing a result of processing performed by the processor circuitry in the processor, the processor circuitry in the processor comprising video signal obtaining processor circuitry, measuring region detector processor circuitry, video pulse wave signal detector processor circuitry, and blood pressure estimating processor circuitry, the method comprising:

obtaining, by the video signal obtaining processor circuitry, the video signal of the predetermined part of the body of the living body from the video camera;

specifying, by the measuring region detector processor circuitry, a part of skin region from which video pulse wave signal in the predetermined part is obtained, from the video signal obtained in the obtaining;

detecting, by the video pulse wave signal detector processor circuitry, first video pulse wave signal from the video signal obtained at a first position of the living body, the first position being included in the specified skin region;

detecting, by the video pulse wave signal detector processor circuitry, second video pulse wave from the video signal obtained at a second position of the living body, the second position being included in the specified skin region and being spaced a distance in a vertical direction from the first position; and estimating, by the blood pressure estimating processor circuitry, the blood pressure of the living body based on:

first pulse wave amplitude, which is a difference between the maximum value and the minimum value within a beat, at the first position obtained from the first video pulse wave signal obtained in the detecting the first video pulse wave signal, second pulse wave amplitude, which is a difference between the maximum value and the minimum value within a beat, at the second position obtained from the second pulse wave signal obtained in the detecting the second video pulse wave signal, and the distance between the first position and the second position in the vertical direction, the method further comprising:

estimating, by the blood pressure estimating processor circuitry, the blood pressure of the living body using an expression $$P=gh/(1-R)+\alpha$$

where, q represents a density; h represents the distance in the vertical direction; R represents a ratio of the first pulse wave amplitude at the first position to the second pulse wave amplitude at the second position; and a represents a bias coefficient.

10. A non-transitory computer-readable recording medium having stored therein a blood pressure estimating program that, when executed by an apparatus for estimating a blood pressure comprising a video camera configured to obtain a video signal of a predetermined part of a body of a living body; a memory; a processor including processor circuitry coupled to the memory; and a display configured to display a video obtained by the video camera and information representing a result of processing performed by the processor circuitry in the processor, processor circuitry in the processor comprising video signal obtaining processor circuitry, measuring region detector processor circuitry, video pulse wave signal detector processor circuitry and blood pressure estimating processor circuitry, causes the processor to execute a process comprising:

obtaining, by the video signal obtaining processor circuitry, the video signal of the predetermined part of the body of the living body from the video camera;

specifying, by the measuring region detector processor circuitry, a part of skin region from which video pulse wave signal in the predetermined part is obtained, from the video signal obtained in the obtaining;

detecting, by the video pulse wave signal detector processor circuitry, first video pulse wave signal from the video signal obtained at a first position of the living body, the first position being included in the specified skin region;

detecting, by the video pulse wave signal detector processor circuitry, second video pulse wave from the video signal obtained at a second position of the living body, the second position being included in the specified skin region and being spaced a distance in a vertical direction from the first position; and estimating, by the blood pressure estimating processor circuitry, the blood pressure of the living body based on:

first pulse wave amplitude, which is a difference between the maximum value and the minimum value within a beat, at the first position obtained from the first video pulse wave signal obtained in the detecting the first video pulse wave signal,

second pulse wave amplitude, which is a difference between the maximum value and the minimum value within a beat, at the second position obtained from the second pulse wave signal obtained in the detecting the second video pulse wave signal, and the distance between the first position and the second position in the vertical direction the process further comprising:

estimating, by the blood pressure estimating processor circuitry, the blood pressure of the living body using an expression $$P = gh/(1-R) + \alpha$$

where, q represents a density; h represents the distance in the vertical direction; R represents a ratio of the first pulse wave amplitude at the first position to the second pulse wave amplitude at the second position; and a represents a bias coefficient.

* * * * *